US00PP33362P2

(12) United States Plant Patent
Davis

(10) Patent No.: US PP33,362 P2
(45) Date of Patent: Aug. 17, 2021

(54) ***TERNSTROEMIA* PLANT NAMED 'CAROLINA SUNSET'**

(50) Latin Name: *Ternstroemia gymnanthera*
Varietal Denomination: Carolina Sunset

(71) Applicant: Richard Davis, Accomal, VA (US)

(72) Inventor: Richard Davis, Accomal, VA (US)

( * ) Notice: Subject to any disclaimer, the term of this patent is extended or adjusted under 35 U.S.C. 154(b) by 0 days.

(21) Appl. No.: 16/995,592

(22) Filed: Aug. 17, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Ternstroemia* plant, 'Carolina Sunset', that is characterized by its unique, brightly colored gold foliage in spring into summer and again on new growth in fall, its easily maintainable plant habit with a plant height of 1.2 to 1.8 m, and its new shoots that are coppery orange in color.

2 Drawing Sheets

Botanical classification: *Ternstroemia gymnanthera.*
Varietal denomination: 'Carolina Sunset'.

BACKGROUND OF THE INVENTION

The present invention relates to a new and distinct cultivar of *Ternstroemia gymnanthera* and will be referred to hereafter by its cultivar name, 'Carolina Sunset'. 'Carolina Sunset' represents a new evergreen shrub grown for landscape use.

'Carolina Sunset' was discovered by the Inventor as a chance seedling amongst seedlings in a production plot planted with seed from unnamed and unpatented plants of *Ternstroemia gymnanthera* in Locustville, Va. in 2001. The exact parent is unknown.

Asexual propagation of the new cultivar was first accomplished by semi-hardwood cuttings in September of 2008 under the direction of the Inventor in Locustville, Va. Asexual propagation by semi-hardwood cuttings has determined that the characteristics of this cultivar have been determined to be stable and are reproduced true to type in successive generations.

SUMMARY OF THE INVENTION

The following traits have been repeatedly observed and represent the characteristics of the new cultivar. The characteristics in combination distinguish 'Carolina Sunset' as a distinct cultivar of *Ternstroemia.*

1. 'Carolina Sunset' exhibits unique, brightly colored gold foliage in spring into summer and again on new growth in fall.
2. 'Carolina Sunset' exhibits an easily maintainable plant habit with a plant height of 1.2 to 1.8 m.
3. 'Carolina Sunset' exhibits new shoots that are coppery orange in color.

The plants in the production block of *Ternstroemia gymnanthera* in which 'Carolina Sunset' was discovered differ from 'Carolina Sunset' in having green foliage. 'Carolina Sunset' can be most closely compared to the *Ternstroemia*

*gymnanthera* cultivars 'Sotall' (U.S. Plant Pat. No. 13,680) and 'Conthery' (U.S. Plant Pat. No. 11,735). 'Sotall' differs from 'Carolina Sunset' in having larger leaves that are green in color. 'Conthery' differs from 'Carolina Sunset' in having new foliage that is bronze in color and mature foliage that is green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by PlantsNouveau (The Inventor's licensing agent that does not sell plants), Southern Living Plants, Plant Development Services, MarkWatch, Mobile Botanical Gardens, and Core Media Concepts.

BRIEF DESCRIPTION OF THE DRAWINGS

The accompanying colored photographs illustrate the overall appearance and distinct characteristics of the new *Ternstroemia*. The photographs were taken of a 4-year-old plant of 'Carolina Sunset' as grown in a garden in Locustville, Va.

The photograph in FIG. 1 provides a side view of a plant of 'Carolina Sunset' in spring.

Figure 1:
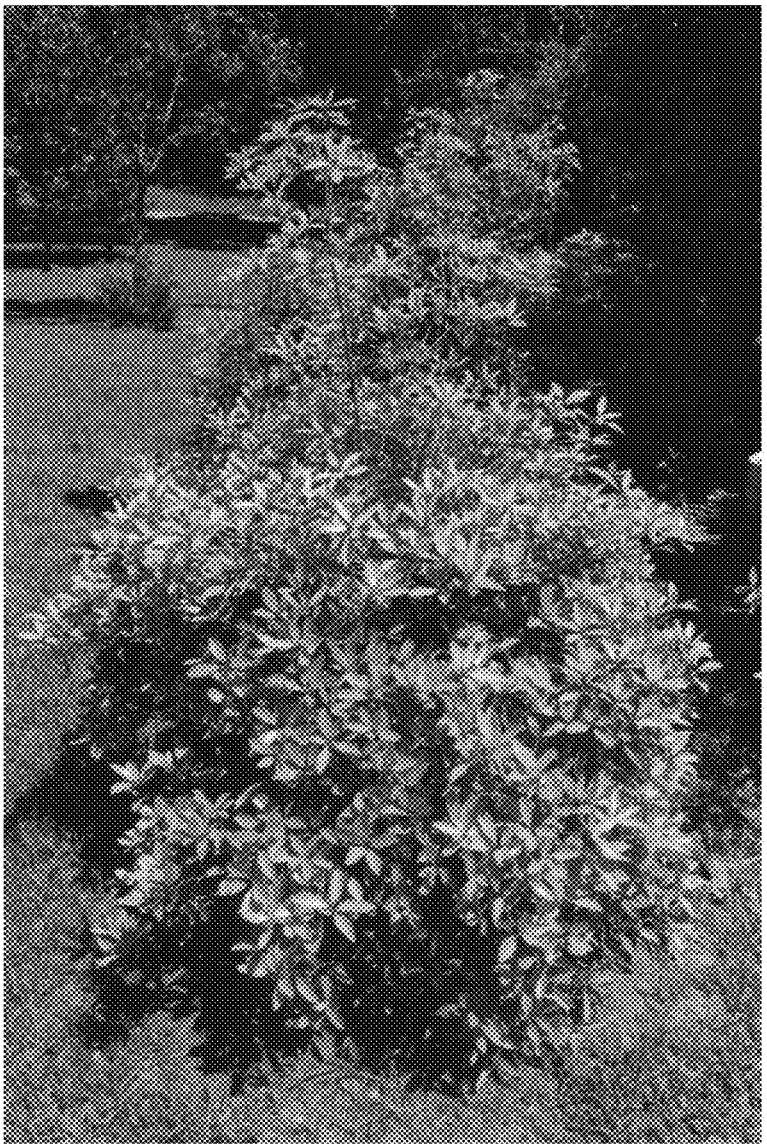
Figure 2:
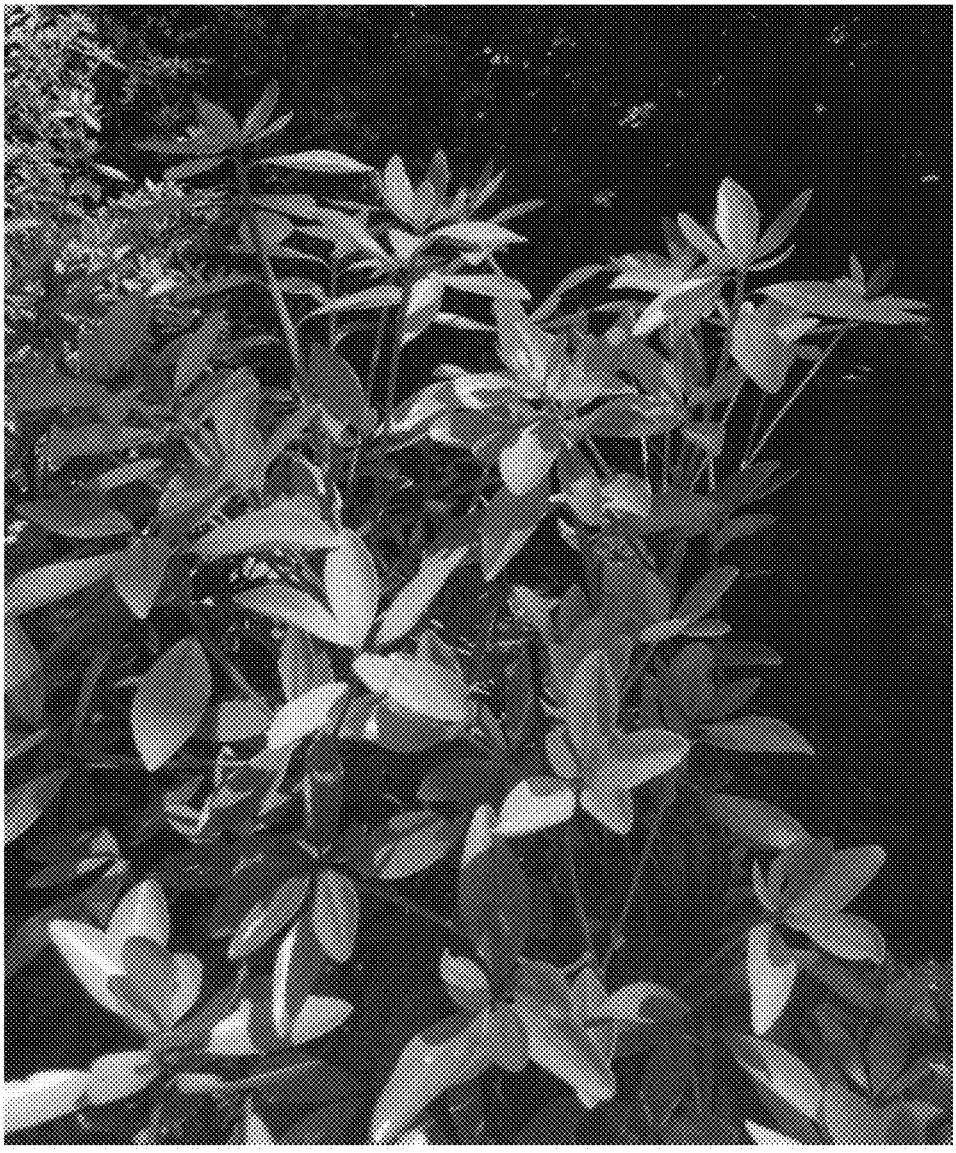

The photograph in FIG. 2 provides a close-up view of the spring foliage of 'Carolina Sunset'.

The colors in the photographs are as close as possible with the photographic and printing technology utilized and color values cited in the detailed botanical description accurately describe the colors of the new *Ternstroemia.*

DETAILED BOTANICAL DESCRIPTION

The following is a detailed description of plants 2-years-in-age as grown outdoors in 2-gallon containers in Locustville, Va. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Blooming period.*—Very sporadic and minimal in May and June in Locustville, Va.

*Plant type.*—Evergreen shrub.

*Plant habit.*—Oval, upright, easily managed in landscape.

*Height and spread.*—Average of 32 cm in height, 45 cm in spread as a 2-year-old plant in a 2-gallon container, mature plants 4 years old in the landscape reach 1.2 to 1.8 m in height and 1.2 to 1.5 m in width.

*Hardiness.*—At least in U.S.D.A. Zones 7 to 10.

*Diseases and pests.*—No resistance or susceptibility to diseases or pests has been observed, no foliage problems have been observed.

*Root description.*—Thick and fleshy and fibrous, 199A in color.

*Propagation.*—Stem cutting and division.

*Growth rate.*—Moderately vigorous.

*Root development.*—2 to 3 years to produce a finished landscape plant.

Stem description:

*Stem shape.*—Rounded.

*Stem color.*—New growth; N144B and 151D, mature stems; 144A, older stems and bark; 199A and N200B in color.

*Stem size.*—Main stem 4 cm in length, 1 cm in diameter, lateral branches 12 cm in length, 5 mm in diameter, tertiary branches 13 cm in length, 3 mm in diameter.

*Stem surface.*—Young stems; smooth, slightly glossy and densely covered with pubescence matching surface color, mature stems and old bark; matte and moderately covered with lenticels; average of 0.5 mm in diameter, 10 per 1 square cm, 156A in color.

*Stem aspect.*—Held in multiple angles branching out from the center.

*Internode length.*—1 to 4 cm.

*Branching.*—Average of 5 lateral branches from main stem.

*Stem strength.*—Strong.

Foliage description:

*Leaf shape.*—Oblanceolate to ovate.

*Leaf division.*—Simple.

*Leaf base.*—Acute.

*Leaf arrangement.*—Whorled or alternate.

*Leaf apex.*—Acute to bluntly acute.

*Leaf aspect* (*curvature*).—Slightly curved downward to horizontal.

*Leaf venation.*—Parallel and inconspicuous, colors match leaf surface colors.

*Leaf margins.*—Entire.

*Leaf size.*—Average of 6 cm in length and up to 2 cm in width.

*Leaf surface.*—Both surfaces glabrous, upper surface very glossy, lower surface matte.

*Leaf number.*—Average of 8 leaves per shoot (varying between 4 and 8).

*Leaf color.*—New shoots upper and lower surface 163A and N163A, young upper surface; a blend of N144A and 3A, base flushed with 176A, young lower surface; a blend of 3A and 146D, base flushed with 176A, mature upper surface; a combination of 147A and 146A, mature lower surface 146D, fall; new growth same coloration as young leaves on upper and lower surface.

*Leaf attachment.*—Mature leaves petiolate, young leaves sessile.

*Petioles.*—(Mature leaves only) an average of 1 cm in length and 2 mm in diameter, glabrous and matte to slightly glossy on upper and lower surfaces, color on new growth; 182A and 184A, color on mature growth and fall/winter; 46A and 53A.

Flower description:

*Flower arrangement and appearance.*—Single inconspicuous cupped flowers, axillary.

*Flower quantity.*—Average of one to three flowers per lateral branch.

*Flower longevity.*—Individual flowers last two to three days on the plant, persistent.

*Fragrance.*—Faint.

*Flower diameter.*—Average of 8 mm to 1 cm.

*Flower depth.*—5 to 6 mm.

*Flower bud.*—Average of 5 mm in length, 4 to 5 mm in diameter, globular in shape, NN155D in color.

*Petals.*—Single whorl of five imbricate petals fused at the base, average of 4 to 4.5 mm in length, 4 to 4.5 mm in width, obtuse in shape, rounded in apex, entire margins, upper and lower surfaces smooth, glabrous and waxy, color; when opening and fully opened, upper and lower surface, NN155C.

*Sepals.*—5, fused into a single whorl, average of 2 mm in length and 2 mm in width, ovate in shape, acute apex, entire margins, upper and lower surfaces smooth, glabrous and waxy, color; young and mature upper and lower surfaces NN155C. Peduncles.—1.5 to 2.5 mm in length, 0.7 to 1.9 mm in diameter, aspect; 45° to 80° from lateral branch axis, strong and flexible, surface is smooth, glabrous and waxy, 157D in color.

Reproductive organs:

*Androecium.*—Stamens; 30 to 40, anthers; oblong in shape, average of 1.5 mm in length, 4C in color, pollen; abundant, 4B in color.

*Gynoecium.*—Pistil; average of 3 mm in length, stigma; bi-lobed, stigma; 149D in color, Style; average of 1 mm in length, style; NN155D in color, ovary; NN155D in color.

*Fruits.*—Quantity per lateral branch; average of 9, about 1 cm in length, 10 mm in diameter, smooth and glabrous surface, 145C in color changing to 46C in color when mature.

*Seed.*—Globose to ovoid in shape, 3 mm in length, 183B in color.

It is claimed:

1. A new and distinct cultivar of *Ternstroemia* plant named 'Carolina Sunset' as herein illustrated and described.

* * * * *